(12) United States Patent
Hyde et al.

(10) Patent No.: US 8,512,679 B2
(45) Date of Patent: Aug. 20, 2013

(54) GLASSY COMPOSITIONS

(75) Inventors: Roderick A. Hyde, Redmond, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 131 days.

(21) Appl. No.: 12/932,781

(22) Filed: Mar. 4, 2011

(65) Prior Publication Data

US 2012/0225011 A1  Sep. 6, 2012

Related U.S. Application Data

(63) Continuation-in-part of application No. 12/932,780, filed on Mar. 4, 2011.

(51) Int. Cl.
*A61K 49/00* (2006.01)

(52) U.S. Cl.
USPC .......................................... 424/10.1; 424/10.3

(58) Field of Classification Search
USPC ......................................................... 424/10.1
See application file for complete search history.

(56) References Cited

U.S. PATENT DOCUMENTS

| | | | |
|---|---|---|---|
| 5,254,473 A * | 10/1993 | Patel ................................ | 436/1 |
| 5,320,845 A | 6/1994 | Py | |
| 6,140,121 A | 10/2000 | Ellington et al. | |
| 6,190,701 B1 | 2/2001 | Roser et al. | |
| 6,290,991 B1 | 9/2001 | Roser et al. | |
| 6,331,310 B1 | 12/2001 | Roser et al. | |
| 6,366,206 B1 * | 4/2002 | Ishikawa et al. ........... | 340/573.1 |
| 6,468,782 B1 | 10/2002 | Tunnacliffe et al. | |
| 6,565,871 B2 | 5/2003 | Roser et al. | |
| 6,586,006 B2 | 7/2003 | Roser et al. | |
| 6,623,762 B2 | 9/2003 | Roser et al. | |
| 6,653,062 B1 * | 11/2003 | DePablo et al. ................ | 435/1.2 |
| 6,669,963 B1 | 12/2003 | Kampinga | |
| 6,689,755 B1 | 2/2004 | Gabel et al. | |
| 6,811,792 B2 | 11/2004 | Roser et al. | |
| 6,841,168 B1 | 1/2005 | Worrall | |
| 6,872,357 B1 | 3/2005 | Bronshtein et al. | |
| 6,893,657 B2 | 5/2005 | Roser et al. | |
| 6,945,952 B2 | 9/2005 | Kwon | |
| 7,056,495 B2 | 6/2006 | Roser et al. | |
| 7,153,472 B1 | 12/2006 | Bronshtein | |
| 7,290,925 B1 | 11/2007 | Skjervold et al. | |
| 7,381,425 B1 | 6/2008 | Truong-Le | |
| 7,713,262 B2 | 5/2010 | Adams et al. | |
| 2001/0038858 A1 | 11/2001 | Roser et al. | |
| 2002/0128599 A1 | 9/2002 | Cormier et al. | |
| 2002/0155129 A1 | 10/2002 | Roser | |
| 2002/0177839 A1 | 11/2002 | Cormier et al. | |
| 2003/0161881 A1 | 8/2003 | Hansen et al. | |
| 2003/0229027 A1 * | 12/2003 | Eissens et al. .................. | 514/23 |
| 2003/0234466 A1 | 12/2003 | Rasmussen et al. | |
| 2004/0049150 A1 | 3/2004 | Dalton et al. | |
| 2004/0082764 A1 * | 4/2004 | Kunz et al. ................. | 530/391.1 |
| 2004/0087893 A1 | 5/2004 | Kwon | |
| 2004/0096455 A1 | 5/2004 | Maa et al. | |
| 2004/0171980 A1 | 9/2004 | Mitragotri et al. | |
| 2004/0228802 A1 * | 11/2004 | Chang et al. ................. | 424/10.2 |
| 2004/0265354 A1 | 12/2004 | Ameri et al. | |
| 2005/0019411 A1 | 1/2005 | Colombo et al. | |
| 2005/0080028 A1 | 4/2005 | Catchpole | |
| 2005/0085434 A1 | 4/2005 | Catchpole | |
| 2005/0123565 A1 | 6/2005 | Subramony et al. | |
| 2005/0197308 A1 | 9/2005 | Dalton et al. | |
| 2005/0277107 A1 | 12/2005 | Toner et al. | |
| 2006/0074376 A1 | 4/2006 | Kwon | |
| 2006/0083690 A1 * | 4/2006 | Chang ......................... | 424/10.2 |
| 2006/0099567 A1 | 5/2006 | Muller-Cohn et al. | |
| 2006/0127415 A1 | 6/2006 | Mayeresse | |
| 2006/0177494 A1 | 8/2006 | Cormier et al. | |
| 2006/0229557 A1 | 10/2006 | Fathallah et al. | |
| 2007/0078376 A1 | 4/2007 | Smith | |
| 2007/0083186 A1 | 4/2007 | Carter et al. | |
| 2007/0110810 A1 | 5/2007 | Smith | |
| 2007/0184096 A1 | 8/2007 | Ameri et al. | |
| 2007/0275467 A1 | 11/2007 | Louvet et al. | |
| 2007/0298052 A1 | 12/2007 | Mayeresse | |
| 2008/0095854 A1 | 4/2008 | Catchpole | |
| 2008/0112915 A1 | 5/2008 | Foldvari et al. | |
| 2008/0125759 A1 | 5/2008 | Konieczynski et al. | |
| 2008/0248098 A1 | 10/2008 | Jin et al. | |
| 2008/0268514 A1 | 10/2008 | Muller et al. | |
| 2008/0294100 A1 | 11/2008 | de Costa et al. | |
| 2009/0011030 A1 | 1/2009 | Jouhikainen et al. | |
| 2009/0035865 A1 | 2/2009 | DeMoor et al. | |
| 2009/0216175 A1 | 8/2009 | Matsumura et al. | |

FOREIGN PATENT DOCUMENTS

WO  WO 2005/113147 A2  12/2005

OTHER PUBLICATIONS

Tetrahydrocannabinol (http://en.wikipedia.org/wiki/THC (downloaded on Dec. 17, 2012)).*
Parabens (http://en.wikipedia.org/wiki/Paraben (downloaded Dec. 17, 2012)).*
Riboflavin (http://en.wikipedia.org/wiki/Riboflavin (downloaded Dec. 17, 2012)).*
Velasco et al (Towards the use of cannabinoids as antitumour agents. Nat Rev Cancer. May 4, 2012;12(6):436-44.).*
De Jonge et al.; "Inulin sugar glasses preserve the structural integrity and biological activity of influenza virosomes during freeze-drying and storage"; European Journal of Pharmaceutical Sciences; Sep. 2007; Abstract; one page; pp. 33-44; vol. 32, Issue 1; located at http://www.sciencedirect.com/science?_ob=ArticleURL&_udi=6T2; printed on Sep. 20, 2010.
Dreaper, Jane; "Fridge-free vaccine hopes raised"; BBC News; bearing a date of Feb. 18, 2010; one page; located at http://news.bbc.co.uk/go/pr/fr/-/2/hi/health/8520825.stm; BBC; printed on Mar. 7, 2011.

(Continued)

*Primary Examiner* — Jake Vu (57) ABSTRACT

Embodiments disclosed herein relate to thermostable storage of one or more therapeutic agents, including at least one detectable indicator. In an embodiment, the one or more therapeutic agents including at least one detectable indicator are included in at least one glassy substance. Also disclosed are embodiments relating to delivery devices for administration of the thermostable therapeutic agents.

21 Claims, 6 Drawing Sheets

(56) References Cited

OTHER PUBLICATIONS

Fernando et al.: "Potent Immunity to Low Doses of Influenza Vaccine by Probabilistic Guided Micro-Targeted Skin Delivery in a Mouse Model"; PLoS One; Apr. 2010; pp. 1-11; vol. 5, Issue 4, e10266; www.plosone.org.

Jones et al.; "Dehydration of trehalose dihydrate at low relative humidity and ambient temperature"; International Journal of Pharmaceutics; Apr. 26, 2006; Abstract; pp. 1-3; vol. 313, Issues 1-2; pp. 87-98; located at http://www.sciencedirect.com/science?_ob=ArticleURL&_udi+B6T; Elsevier B. V.; printed on Aug. 24, 2010.

Jonietz, Erika; "Vaccines that Can Beat the Heat"; Technology Review; Feb. 18, 2010; pp. 1-2; located at http://www.technologyreview.com/printer_friendly_article.aspx?id=24603; MIT; printed on Mar. 7, 2011.

Koster et al.: "Effects of Vitrified and Nonvitrified Sugars on Phosphatidylcholine Fluid-to-Gel Phase Transitions"; Biophysical Journal; Apr. 2000; pp. 1932-1946; vol. 78, No. 4; Biophysical Society.

Koster, Karen L.; "Glass Formation and Desiccation Tolerance in Seeds—Communication"; Plant Physiol.; 1991; pp. 302-304; vol. 96.

Kuno et al.; "Evaluation of Rapidly Disintegrating Tablets Manufactured by Phase Transition of Sugar Alcohols"; J Control Release; Jun. 20, 2005; Abstract; one page; pp. 16-22; vol. 105, No. 1-2; located at http://www.ncbi.nlm.nih.gov/pubmed/15955365; printed on Sep. 20, 2010.

Peacock et al.; "The Use of Sequestering Agents for Chemical Cleaning At Ubombo Sugar"; Proc. S. Afr. Sug. Technol. Ass; 1999; pp. 219-224; vol. 73.

Song et al.; "Microneedle Delivery of H5N1 Influenza Virus-Like Particles to the Skin Induces Long-Lasting B- and T-Cell responses in Mice"; Clinical and Vaccine Immunology; Sep. 2010; pp. 1381-1389; vol. 17, No. 9; American Society for Microbiology.

Sun et al.; "Stability of Dry Liposomes in Sugar Glasses"; Biophysical Journal; Apr. 1996; pp. 1769-1776; vol. 70; Biophysical Society.

Surana et al.; "Effect of Preparation Method on Physical Properties of Amorphous Trehalose"; Pharmaceutical Research; Abstract; one page; pp. 1167-1176; vol. 21, No. 7; DOI: 10.1023/B:PHAM.0000033003.17251.c3; located at http://www.springerlink.com/content/w176vu031304w311/abstract/?ta; printed on Aug. 24, 2010.

Adams et al.; "Microfluidic integration on detector arrays for absorption and fluorescence micro-spectrometers"; Sensors and Actuators A; 2003; pp. 25-31; vol. 104; Elsevier Science B.V.

Alcock et al.; "Long-Term Thermostabilization of Live Poxviral and Adenoviral Vaccine Vectors at Supraphysiological Temperatures in Carbohydrate Glass"; Science; Feb. 17, 2010; pp. 1-8; vol. 2, Issue 19 19ra12.

Amorij et al.; "Rational design of an influenza subunit vaccine powder with sugar glass technology: Preventing conformational changes of haemagglutinin during freezing and freeze-drying"; Vaccine; 2007; pp. 6447-6457; vol. 25; Elsevier Ltd.

Fields et al.; "Hot spots in cold adaptation: Localized increases in conformational flexibility in lactate dehydrogenase $A_4$ orthologs of Antarctic notothenioid fishes"; Proc. Natl. Acad. Sci. USA; Sep. 1998; pp. 11476-11481; vol. 95.

Hanke et al.; "Clinical experience with plasmid DNA- and modified vaccinia virus Ankara-vectored human immunodeficiency virus type 1 clade A vaccine focusing on T-cell induction"; Journal of General Virology; 2007; pp. 1-12; vol. 88, SGM.

Liu et al.; "A facile 'liquid molding' method to fabricate PDMS microdevices with 3-dimensional channel topography"; Lab Chip; May 7, 2009; Abstract; one page; pp. 1200-1205; vol. 9, No. 9.

Nisselbaum et al.; "Purification, Kinetic, and Immunochemical Studies of the Major Variants of Lactic Dehydrogenase from Human Liver, Hepatoma, and Erythrocytes; Comparison with the Major Variant of Human Heart Lactic Dehydrogenase"; The Journal of Biological Chemistry; Mar. 1963; pp. 969-974; vol. 238, No. 3.

Unger et al.; "Monolithic Microfabricated Valves and Pumps by Multilayer Soft Lithography"; Science; Apr. 7, 2000; pp. 113-116; vol. 288.

* cited by examiner

400 A system comprising:

410 a device including a housing configured for receiving and retaining a reservoir; the reservoir configured for receiving and retaining a composition, the composition including a glassy substance including at least one therapeutic agent and at least one detectable indicator; and a sensor configured for sensing activation of the at least one detectable indicator 420 further comprising a transmitter for transmitting information related to activation of the at least one detectable indicator 430 further comprising a receiver for receiving information related to activation of the at least one detectable indicator 440 further comprising a processor for processing information received related to activation of the at least one detectable indicator 450 wherein the processor includes at least one computing device 460 wherein at least two of the sensor, transmitter, or receiver are configured to form a feedback loop based on information related to activation of the at least one detectable indicator 470 wherein the device is disabled based on information related to activation of the detectable indicator

GLASSY COMPOSITIONS

RELATED APPLICATIONS

For purposes of the USPTO extra-statutory requirements, the present application constitutes a continuation-in-part of U.S. patent application Ser. No. 12/932,780, entitled GLASSY COMPOSITIONS, naming Michael Hartmann Baym, Roderick A. Hyde, Muriel Y. Ishikawa and Lowell L. Wood, Jr. as inventors, filed 4 Mar. 2011, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related applications") (e.g., claims earliest available priority dates for other than provisional patent applications or claims benefits under 35 USC §119(e) for provisional patent applications, for any and all parent, grandparent, great-grandparent, etc. applications of the Related application(s)). All subject matter of the Related applications and of any and all parent, grandparent, great-grandparent, etc. applications of the Related applications is incorporated herein by reference to the extent such subject matter is not inconsistent herewith.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In an embodiment, the disclosure relates to a composition, and a kit relating thereto, including a glassy substance including at least one therapeutic agent; and at least one detectable indicator configured to indicate degradation or disruption of the glassy substance. In an embodiment, a device, comprises a housing configured for receiving and retaining at least two reservoirs; the at least two reservoirs configured for receiving and retaining a composition, the composition including a glassy substance including at least one therapeutic agent. In an embodiment, a system, comprises a device including a housing configured for receiving and retaining a reservoir; the reservoir configured for receiving and retaining a composition, the composition including a glassy substance including at least one therapeutic agent and at least one detectable indicator; and a sensor configured for sensing activation of the at least one detectable indicator. In an embodiment, a system comprises a computing device configured for processing data relating to at least one of the storage, tracking, or analysis of a composition including a glassy substance, the glassy substance including at least one therapeutic agent and at least one detectable indicator.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Thermostable storage of therapeutic agents (e.g., biological agents) allows for increased lifespan for use of the therapeutic agents. For example, mixing virus-based vaccines with one or more sugar glassy substances and drying on filter paper allows for increased stability for longer time periods, even at higher temperatures. In an embodiment, oral polio virus vaccine, or another viral vaccine, is mixed with one or more sugar glassy substances and allowed to dry on filter paper (e.g., air dry, desiccate, freeze dry, spray dry, etc.). In an embodiment, male or female gametes are mixed with one or more glassy substances, and dried onto filter paper. In an embodiment, oocytes are vitrified in trehalose glass.

In an embodiment, the one or more glassy substances are coated with strands of micro-diameter material (e.g., "cotton candy strands"), in order to provide for a high surface area for rapid drying action and compact storage.

In an embodiment, the glassy substance itself can be coated on a substrate (e.g., sheet, fiber, particle, etc.).

In an embodiment, one or more therapeutic agent bundles are packaged inside a degradable coating, for example, so that it can be implanted into a subject (e.g., human, other animal, plant, etc.) and stored within the subject until needed. For example, the implant can be just beneath the exterior of the subject (e.g., subcutaneously, subdermally, etc.), and the coating can further be degraded upon a factor (e.g., external command, time interval, local inflammation, etc.).

In an embodiment, the reconstitution fluid includes at least one of water, saline, buffer (e.g., HEPES, Ringer's, etc.), biological fluid (e.g., saliva, blood, etc.), oil, or other non-toxic fluid.

In an embodiment, the glassy substance includes at least one of a disaccharide, or oligosaccharide. In an embodiment, the glassy substance includes at least one of sucrose, glucose, fructose, maltose, mannose, maltulose, iso-maltose, nigerose, cellubiulose, turanose, panose, isomaltotriose, stachyose, nystose, maltotetrose, maltopentose, maltohexose, maltopheptose, ubombo sugar, raffinose, arabinose, galactose, xylose, melibiose, salicin, esculin, arbutin, glycerol, arabinose, adonitol, sorbose, thamnose, dextrose, inulin, dextran, malto-dextran, dulcitol, melezitose, starch, glycogen, gentiobiose, lyxose, tagatose, fucose, arabitol, gluconate, or trehalose. In an embodiment, the glassy substance includes at least one non-reducing monosaccharide (e.g., methylated version). In an embodiment, the glassy substance includes at least one of carboxylate, phosphate, nitrate, sulfate, or bisulfate.

In an embodiment, the glassy substance includes at least one of an amino acid glass, sugar glass, metal carboxylate glass, borosilicate glass, acrylic glass, aluminum oxynitride glass, Muscovite glass, or calcium phosphate glass. In an embodiment, the glassy substance includes at least one of dextran, phosphatidylcholine, hexuronic acid, or polyethylene glycol. In an embodiment, the glassy substance includes at least one sugar alcohol. In an embodiment, the sugar alcohol includes at least one of sorbitol, mannitol, inositol, erythritol, or lactitol. In an embodiment, the glassy substance includes at least one of palatnitol, xylitol, glucopyranosyl sorbitol, or glucopyranosyl mannitol.

In an embodiment, the glassy substance is spun into fibers (e.g., "cotton candy") for storage or delivery. The fibers can be cut after formation of the solution or mixture, and before or after enclosure in the delivery device.

In an embodiment, the therapeutic agent includes at least one of a vaccine, adjuvant, small molecule (peptide, protein, hormone, nucleic acid, antibody or antibody fragments, etc.), biological agent (bacteria, virus, eukaryotic or prokaryotic cell, liposome, phage, etc.). In an embodiment, the therapeutic agent includes at least one of an organic or inorganic small molecule, clathrate or caged compound, protocell, coacervate, microsphere, proteinoid, liposome, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, glycoprotein, sphingolipid, glycosphingolipid, peptidoglycan, lipid, carbohydrate, metalloprotein, proteoglycan, chromosome, nucleus, nitric oxide, nitric oxide synthase, amino acid, micelle, polymer, co-polymer, or piloxymer.

In at least one embodiment, the at least one therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, chemical debridement agent, immunogen, antigen, radioactive agent, apoptotic promoting factor, angiogenic factor, anti-angiogenic factor, hormone, enzymatic factor, enzyme, papain, collagenase, protease, peptidase, elastase, urea, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In at least one embodiment, the nutraceutical includes one or more of a flavonoid, antioxidant, beta-carotene, anthocyanin, alpha-linolenic acid, omega-3 fatty acids, yeast, bacteria, algae, other microorganisms, plant products, or animal products. In at least one embodiment, the analgesic or anesthetic includes one or more of any aminoamid or aminoester local anesthetic, ibuprofen, morphine, codeine, aspirin, acetaminophen, lidocaine/lignocaine, ropivacaine, mepivacaine, benzocaine, chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, piperocaine, prilocalne, trimecaine, saxitoxin, or tetrodotoxin.

In at least one embodiment, the therapeutic agent includes at least one anti-inflammatory agent, including but not limited to steroids, non-steroidal anti-inflammatory drugs, topical anti-inflammatory agents, or subcutaneously administered non-steroidal anti-inflammatory drugs (e.g. diclofenac).

In at least one embodiment, the analgesic includes but is not limited to one or more of paracetamol (acetaminophen), non-steroidal anti-inflammatory drugs (NSAIDs), salicylates, narcotics, or tramadol. In at least one embodiment, the analgesic includes but is not limited to aspirin, rofecoxib, celecoxib, morphine, codeine, oxycodone, hydrocodone, diamorphine, pethidine, buprenorphine, amitriptyline, carbamazepine, bagapentin, pregabalin, ibuprofen, naproxen, lidocaine, a psychotropic agent, orphenadrine, cyclobenzaprine, scopolamine, atropine, gabapentin, methadone, ketobemidone, fentanyl, or piritramide.

In at least one embodiment, the at least one therapeutic agent includes one or more antiseptic, including but not limited to one or more of an alcohol, a quaternary ammonium compound, boric acid, hydrogen peroxide, chlorhexidine gluconate, iodine, mercurochrome, octenidine dihydrochloride, phenol (carbolic acid) compounds, sodium chloride, or sodium hypochlorite.

In at least one embodiment, the antiseptic includes but is not limited to one or more of povidone-iodine, iodine, ethanol, 1-propanol, 2-propanol/isopropanol, benzalkonium chloride, cetyl trimethylammonium bromide, cetylpyridinium chloride, benzethonium chloride, chlorhexidine, octenidine dihydrochloride, or carbolic acid.

In at least one embodiment, the antimicrobial agent includes at least one of an anti-fungal agent, antibiotic agent, anti-bacterial, anti-parasitic agent, or anti-worm agent. In certain instances, the antimicrobial agent may occur in nature, or it may be synthetic.

In at least one embodiment, the at least one therapeutic agent includes one or more anti-tumor agent, at least one of which may also be identified as a cytotoxic agent, or chemotherapy agent. Non-limiting examples of an anti-tumor agent for use as described herein include at least one of an alkylating agent, antimetabolite, anthracycline, plant alkaloid (such as paclitaxel), topoisomerase inhibitor, monoclonal antibody, or tyrosine kinase inhibitor. In at least one embodiment, the therapeutic agent includes one or more of imatinib, mechlorethamine, cyclophosphamide, chlorambucil, azathioprine, mercaptopurine, vinca alkaloid, taxane, vincristine, vinblastine, vinorelbine, vindesine, podophyllotoxin, etoposide, teniposide, amsacrine, dactinomycin, trastuzumab, cetuximab, rituximab, bevacizumab, dexamethasone, finasteride, tamoxifen, goserelin, telomerase inhibitor, dichloroacetate, aminopterin, methotrexate, pemetrexed, raltitrexed, cladribine, clofarabine, fludarabine, pentostatin, thioguanine, cytarabine, decitabine, fluorouracil/capecitabine, floxuridine, gemcitabine, enocitabine, sapacitabine, chloromethine, cyclophosphamide, ifosfamide, melphalan, bendamustine, trofosfamide, uramustine, carmustine, fotemustine, lomustine, nimustine, prednimustine, ranimustine, semustine, spretpozocin, carboplatin, cisplatin, nedaplatin, oxaliplatin, triplatin tetranitrate, satraplatin, busulfan, mannosulfan, treosulfan, procarbazine, decarbazine, temozolomide, carboquone, ThioTEPA, triaziquone, triethylenemelamine, docetaxel, larotaxel, ortataxel, tesetaxel, vinflunine, ixabepilone, aclarubicin, daunorubicin, doxorubicin, epirubicin, idarubicin, amrubicin, pirarubicin, valrubicin, zorubicin, metoxantrone, pixantrone, actinomycin, bleomycin, mitomycin, plicamycin, hydroxyurea, camptothecin, topotecan, irinotecan, rubitecan, belotecan, altretamine, amsacrine, bexarotene, estramustine, irofulven, trabectedin, cetuximab, panitumumab, trastuzumab, rituximab, tositumomab, alemtuzumab, bevacizumab, edrecolomab, gemtuzumab, axitinib, bosutinib, cediranib, dasatinib, erlotinib, gefitinib, imatinib, lapatinib, lestaurtinib, nilotinib, semaxanib, sorafenib, sunitinib, vandetanib, alvocidib, seliciclib, aflibercept, denileukin diftitox, aminolevulinic acid, efaproxiral, porfimer sodium, talaporfin, temoporfin, verteporfin, alitretinoin, tretinoin, anagrelide, arsenic trioxide, asparaginase/ pegaspergase, atrasentan, bortezomib, carmofur, celecoxib, demecolcine, elesclomol, elasamitrucin, etoglucid, lonidamine, lucanthone, masoprocol, mitobronitol, mitoguanzone, mitotane, oblimersen, omacetaxine, sitimagene ceradenovec, tegafur, testolactone, tiazofurine, tipifarnib, or vorinostat.

In at least one embodiment, at least one nutraceutical is included. At least one nutraceutical includes but is not limited to one or more of an extract of plant or animal matter (e.g., an oil, aqueous, or solid extract), a vitamin, a mineral, a mixture or solution, a food supplement, a food additive, a food fortification element, or other nutraceutical. In at least one embodiment, at least one nutraceutical includes but is not limited to resveratrol, an antioxidant, psyllium, sulforaphane, isoflavonoid, alpha-linolenic acid, beta-carotene, anthocyanins, phytoestrogens, polyphenols, polyphenons, catechins, benzenediols, tannins, phenylpropanoids, caffeine, alcohol, or others.

In at least one embodiment, at least one therapeutic agent includes one or more vaccine. In at least one embodiment, the therapeutic composition including at least one vaccine includes at least one prophylactic vaccine or therapeutic vaccine. In at least one embodiment, the at least one therapeutic vaccine includes at least one anti-cancer vaccine. In at least one embodiment, the at least one vaccine includes at least one of an anti-tumor agent, antimicrobial agent, anti-viral agent, immunogen, antigen, live microbe, dead microbe, attenuated microbe, microbe or component thereof, live virus, recombinant virus, killed virus, attenuated virus, virus component, plasmid DNA, nucleic acid, amino acid, peptide, protein, glycopeptide, proteoglycan, glycoprotein, glycolipid, sphingolipid, glycosphingolipid, cancer cell or component thereof, organic or inorganic small molecule, or toxoid.

One or more vaccine may include but not be limited to vaccines containing killed microorganisms (such as vaccines for flu, cholera, bubonic plague, and hepatitis A), vaccines containing live, attenuated virus or other microorganisms (such as vaccines for yellow fever, measles, rubella, and mumps), live vaccine (such as vaccines for tuberculosis), toxoid (such as vaccines for tetanus, diphtheria, and crotalis atrox), subunit of inactivated or attenuated microorganisms (such as vaccines for HBV, VLP, and HPV), conjugate vaccines (such as vaccines for *H. influenzae* type B), recombinant vector, DNA vaccination. In at least one embodiment, the at least one vaccine includes but is not limited to rubella, polio, measles, mumps, chickenpox, typhoid, shingles, hepatitis A, hepatitis B, diphtheria, pertussis, rotavirus, influenza, meningococcal disease, pneumonia, tetanus, rattlesnake venom, virus-like particle, or human papillomavirus, or anti-cancer vaccine.

In at least one embodiment, the at least one therapeutic agent includes at least one adjuvant. The at least one adjuvant may include but not be limited to one or more organic or inorganic compounds. The at least one adjuvant may include but not be limited to at least one of a liposome, virosome, lipid, phospholipid, mineral salt, single-stranded DNA, double-stranded RNA, lipopolysaccharide, molecular antigen cage, CpG motif, microbial cell wall or component thereof, squalene, oil emulsion, surfactant, saponin, isolated microbial toxin, modified microbial toxin, endogenous immunomodulator, or cytokine.

In an embodiment, the solution or mixture including at least one glassy substance is produced with multiple layers (e.g., a composition of layers of different therapeutic agents and/or different glassy substances). For example, a layered glassy substance composition includes at least two different layers (e.g., including one type of antibody in one layer and another type of antibody in another) to a particular pathogen. In an embodiment, the layered glassy substance composition is implanted into a subject, and the various layered therapeutic agents (e.g., antibodies) are released as the layers of glassy substance(s) decay or are dissolved by the subject's fluid or cells. Thus, in an embodiment, a layered glassy substance composition allows for extended or time release of at least one therapeutic agent. In an embodiment, the reconstitution of the sugar glass occurs as a carrier fluid flows through the reservoir, and out through the applicator. Thus, in an embodiment, no separate reconstitution step is required for administration of the therapeutic agent to a subject.

In an embodiment, at least one detectable indicator is included in one or more glassy substance compositions disclosed herein. In an embodiment, the at least one detectable indicator permit detection of degradation of at least one characteristic of the composition, which includes, for example, functional or structural change in the therapeutic agent or another component of the composition, an intermediate of at least one component of the composition, or the composition as a whole. In an embodiment, the at least one detectable indicator is configured to detect at least one of an amine, alcohol, aldehyde, water, thiol, sulfide, nitrite, avidin, biotin, enzyme, immunoglobulin, oligosaccharide, polypeptide, nucleic acid, cytoskeletal component, reactive oxygen species, metal ion, pH, sodium, potassium, chloride, cyanide, phosphate, selenium, microbial component, temperature, exposure to radiation, or overall integrity of the glassy substance. For example, in an embodiment the detectable indicator includes at least one visual indicator (e.g., fluorescent, luminescent, colorimetric, enzymatic, affinity label, enzyme substrate, phosphorescent, etc.) or at least one electronic indicator can be used to identify the integrity or quality of the therapeutic agent(s) of the glassy substance composition. In an embodiment, the electronic indicator includes at least one radio frequency identification tag.

In an embodiment, the detectable indicator is at least one of non-toxic, biodegradable, or biocompatible.

In an embodiment, the detectable indicator is activated by a physical action including, but not limited to, pressure variation, temperature variation, or variation in wavelength exposure to radiation. Examples of detectable indicators can be found, for example, in U.S. Patent App. Pub. No. 2007/ 0275467; and U.S. Pat. No. 7,290,925; each of which is incorporated herein by reference.

In an embodiment, the detectable indicator includes at least one glassy substance. Thus, in an embodiment, the detectable indicator itself is a glassy substance. In an embodiment, the detectable indicator is included in a glassy substance that is separate or distinct from the glassy substance of the therapeutic agent. In an embodiment, the glassy substance of the detectable indicator has a structural or chemical integrity that is less than that of the glassy substance including the at least one therapeutic agent. For example, in an embodiment, the glassy substance of the detectable indicator has a hardness that is less than the glassy substance including the at least one therapeutic agent. In an embodiment, the glassy substance of the detectable indicator liquefies at a lower temperature or pressure than the glassy substance of the therapeutic agent. In an embodiment, the glassy substance of the detectable indicator degrades under conditions less stringent than the glassy substance of the therapeutic agent. In an embodiment, at least one optical property of the glassy substance is altered at less stringent conditions than the glassy substance of the therapeutic agent. For example, the glassy substance as a detectable indicator can include a change in color or opacity, as determined by monitoring the optical transmittance or reflectance of the glassy substance. In an embodiment, a rate-controlling substance is utilized with at least one of the glassy substance of the detectable indicator or the glassy substance of the therapeutic agent. For example, non-reducing sugars, or natural or synthetic polymers (gelatin, PVP, etc.) can be added to the glassy substance.

In an embodiment, the composition can be part of a sample storage and management system, for example by recording or testing the sample at the original source, or at least one point along the chain of handling, delivering, or utilizing the composition. An example of such a sample storage and management system that is integrated with the compositions described herein is described, for example, in WO 2005/113147, which is incorporated herein by reference.

In an embodiment, the composition includes at least one carrier fluid. In an embodiment, the at least one carrier fluid includes at least one phase of one or more of water, saline, intravenous fluid (or other biological fluid), or other fluid.

In an embodiment, the composition further includes at least one preservative. In an embodiment, the at least one preservative includes at least one enzyme inhibitor. In an embodiment, the at least one preservative includes at least one of validamycin A, TL-3, sodium orthovanadate, sodium fluoride, N-alpha-tosyl-Phe-chloromethylketone, N-alpha-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In an embodiment, the composition further includes at least one buffer. In an embodiment, the at least one buffer includes at least one of bicarbonate, monosodium phosphate, disodium phosphate, or magnesium oxide.

Figure 1:
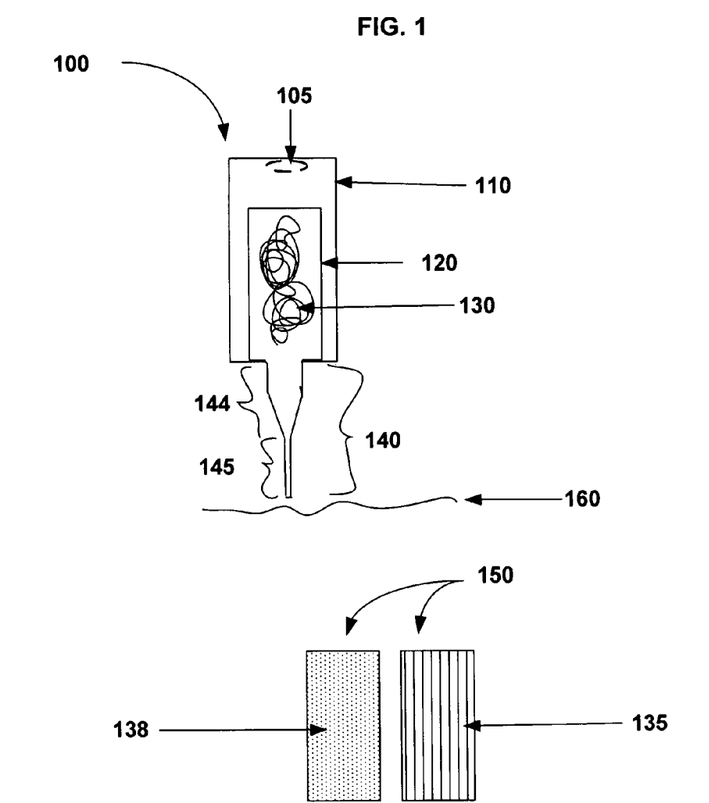
FIG. 1 is a partial view of a cross-section of an embodiment disclosed herein.

Referring now to the Figures, FIG. 1 illustrates an embodiment of a delivery device 100 disclosed herein. In an embodiment, the delivery device 100 includes at least one of a syringe, ear dropper, eye dropper, bronchial inhaler, nasal dropper or inhaler, transdermal patch, transdermal jet, or other device.

For example, in an embodiment, a glassy substance includes sugar glass containing at least one therapeutic agent in a reservoir 120, for example used in a delivery device 100, for reconstitution by a non-toxic fluid. In an embodiment, the device includes a port 105 to allow introduction of a fluid for reconstitution of the therapeutic agent. In an embodiment, the delivery device 100 includes an applicator 140 that allows for administration of the fluid, glassy substance, and therapeutic agent suspension or solution into a subject 160. In an embodiment, the glassy substance reservoir 120 is integrally connected with the delivery device 100. In an embodiment, the glassy substance reservoir 120 is separate. In an embodiment the glassy substance reservoir 120 is modular and can be connected prior or during application to a subject 160. For example, in an embodiment the delivery device 100 includes multiple modular reservoirs 150 for storage or delivery of the therapeutic agent(s).

In an embodiment, fluid flow occurs from one modular reservoir to another (e.g., in serious or in parallel, etc.) (not shown). In an embodiment, a fraction of the fluid flows from one modular reservoir to another. In an embodiment, the flow from one reservoir to another can be designed for a given direction through the reservoirs (e.g., in order to reconstitute particular therapeutic agents in a given order), or for a given time (e.g., time variability, or sufficient time to allow for post-reconstitution reaction).

In an embodiment, a modular reservoir holds different amounts of material (e.g., therapeutic agent, glassy substance, etc.). In an embodiment, the modular reservoir can be used to allow for a desired dosage to be achieved by a combination of two or more standardized reservoirs (e.g., 1.5 g, by combining a 1.0 g reservoir with a 0.5 g reservoir). In an embodiment, standardized dosage reservoirs can have predefined dosage relationships with each other (e.g., 1×, 2×, 4×, 8×, etc.) to allow for combinatorial attainment of non-standardized dosages.

In an embodiment, the delivery device reservoirs 120 can be designed to hold specific therapeutic dosages. For example, two or more reservoirs can hold the same therapeutic agent, with multiple reservoirs (e.g., by binary combination) to determine the overall dosage, as well as absolute or relative dosage of one or more therapeutic agent(s).

In an embodiment, the delivery device 100 can include a syringe and/or needle 145. In an embodiment, the glassy substance reservoir 120 is located between the syringe and needle (if present) such that the syringe can contain the fluid and be used to deliver fluid into the glassy substance for reconstitution. In an embodiment, these components are connected as a single unit. In an embodiment, the components are modular and changeable. For example, the syringe can puncture the glassy substance reservoir 120, compressing the glassy substance fibers while delivering the fluid (not shown).

In an embodiment, the delivery device can include various iterations and modes for delivering the therapeutic agent to a subject 160 (e.g., to an orifice, skin, or other tissue location including but not limited to eye, nose, mouth, etc.).

In an embodiment, a carrier fluid contacts the glassy substance including the therapeutic agent and detectable indicator, thereby dissolving or dispersing the glassy substance and one or more of its components into solution or suspension. Upon expression of the delivery device, the carrier fluid containing the glassy substance and its components is released from the device. In this manner, the therapeutic agent can be administered to a subject. In an embodiment, the glassy substance and its components is in the form of filaments 130 (e.g., "cotton candy" strands) within a reservoir 120 of the housing 110 of the delivery device 100. In an embodiment, the delivery device 100 can be utilized with one or more reservoirs 120. In an embodiment, each reservoir 150 is modular and can be inserted or removed from the delivery device 100. In an embodiment, a reservoir 120 is continuous with the delivery device housing 110 and cannot be separated from the device. In an embodiment, a needle 145 or other tool is included in the administration portion 140 of the delivery device 100. In an embodiment, a needle 145 is optional, such that a needless applicator 144 is utilized (e.g., ear dropper, eye dropper, etc.) for administration to a subject 160. In an embodiment, the glassy substance 130 including the therapeutic agent and detectable indicator is bound to a matrix (not shown) within the reservoir 120. In an embodiment, the glassy substance 130 is unbound, and is contained within the reservoir 120 of the housing 110. In an embodiment, multiple reservoirs 150 can each contain a different dosage of a particular therapeutic agent, or a different therapeutic agent, for example.

Figure 2:
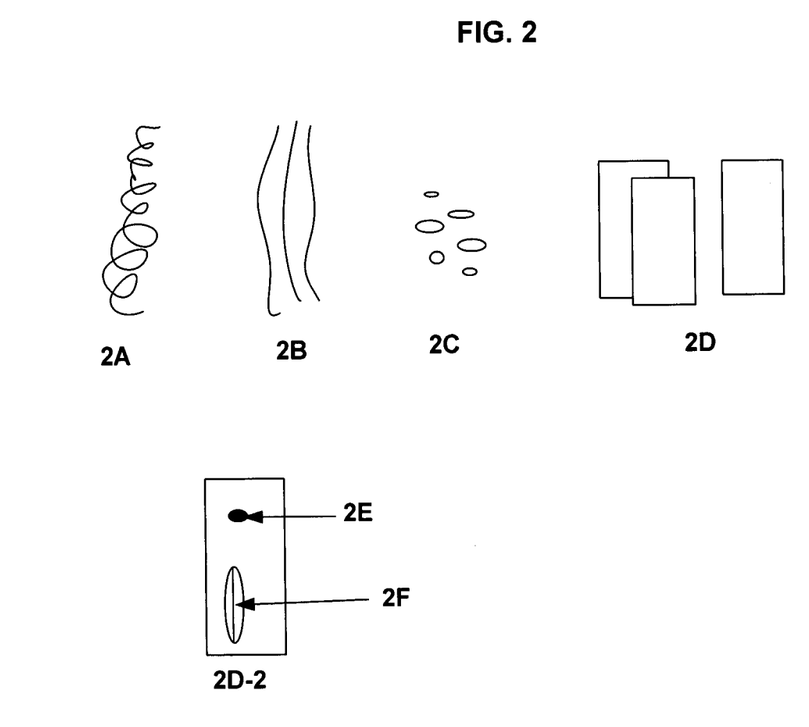
FIG. 2 is a partial view of particular embodiments disclosed herein.

Turning to FIG. 2, in one embodiment, the glassy substance and its components is in the form of particles 2C. In an embodiment, the glassy substance and its components is in the form of filaments (e.g., "cotton candy" 2A, strands 2B), or sheets 2D. For example, FIG. 2 illustrates a glassy substance sheet 2D-2 including at least one therapeutic agent 2F, at least one detectable indicator 2E.

Figure 3:
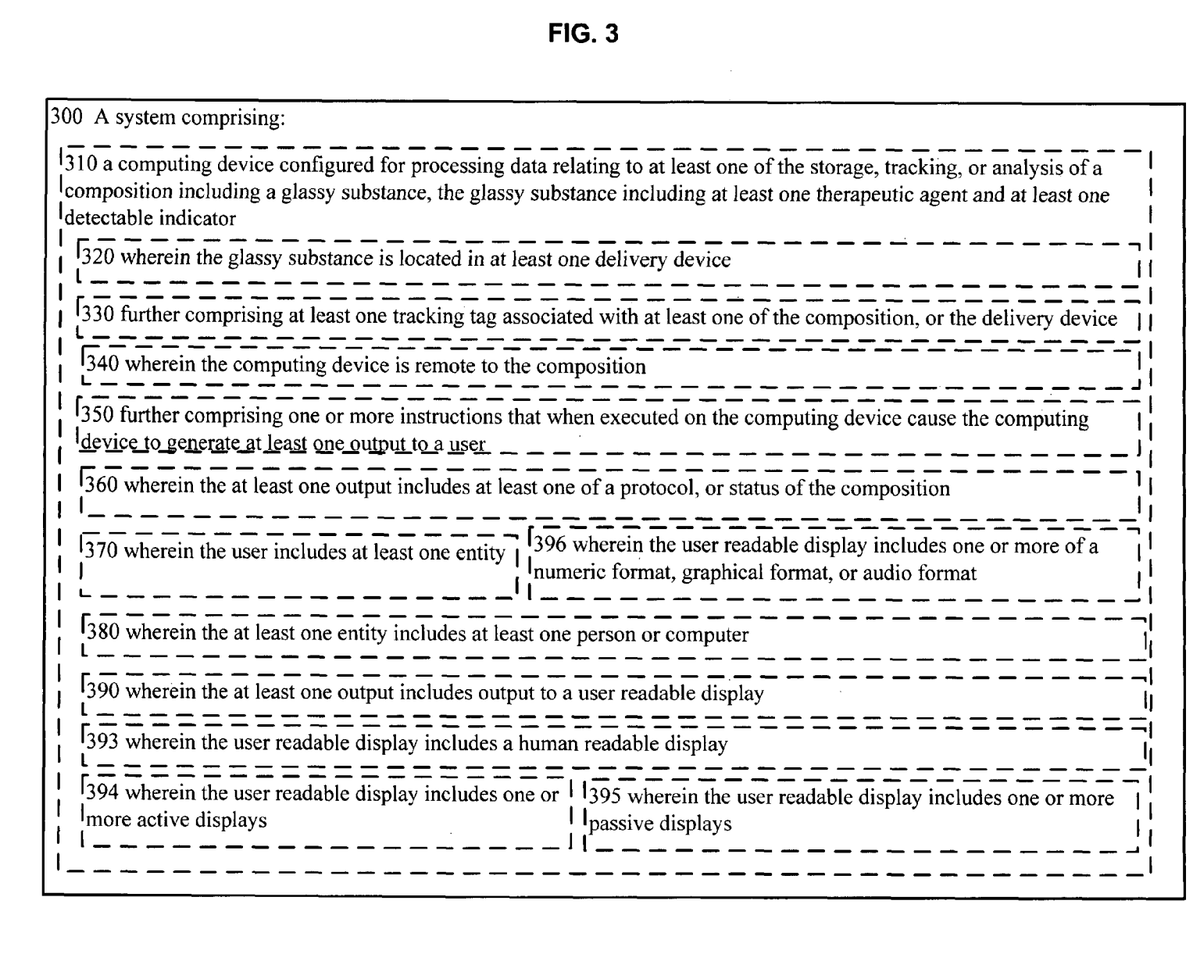
FIG. 3 is a partial view of an embodiment of a system disclosed herein.

As illustrated in FIG. 3, in an embodiment, a system 300 including 310 a computing device configured for processing data relating to at least one of the storage, tracking, or analysis of a composition, including a glassy substance, the glassy substance including at least one therapeutic agent and at least one detectable indicator. In an embodiment 320 the glassy substance is located in at least one delivery device. In an embodiment 330, the system further comprises at least one tracking tag associated with at least one of the composition or the delivery device. In an embodiment 340, the computing device is remote to the composition. In an embodiment 350, the system further comprises one or more instructions that when executed on the computing device cause the computing device to generate at least one output to a user. In an embodiment 360, the at least one output includes at least one of a protocol, or status of the composition. In an embodiment 370, the user includes at least one entity. In an embodiment 380 the at least one entity includes at last one person or computer. In an embodiment 390, the at least one output includes output to a user readable display. In an embodiment 393, the user readable display includes a human readable display. In an embodiment 394, the user readable display includes one or more active displays. In an embodiment 395, the user readable display includes one or more passive displays. In an embodiment 396, the user readable display includes one or more of a numeric format, graphical format, or audio format.

Figure 4:
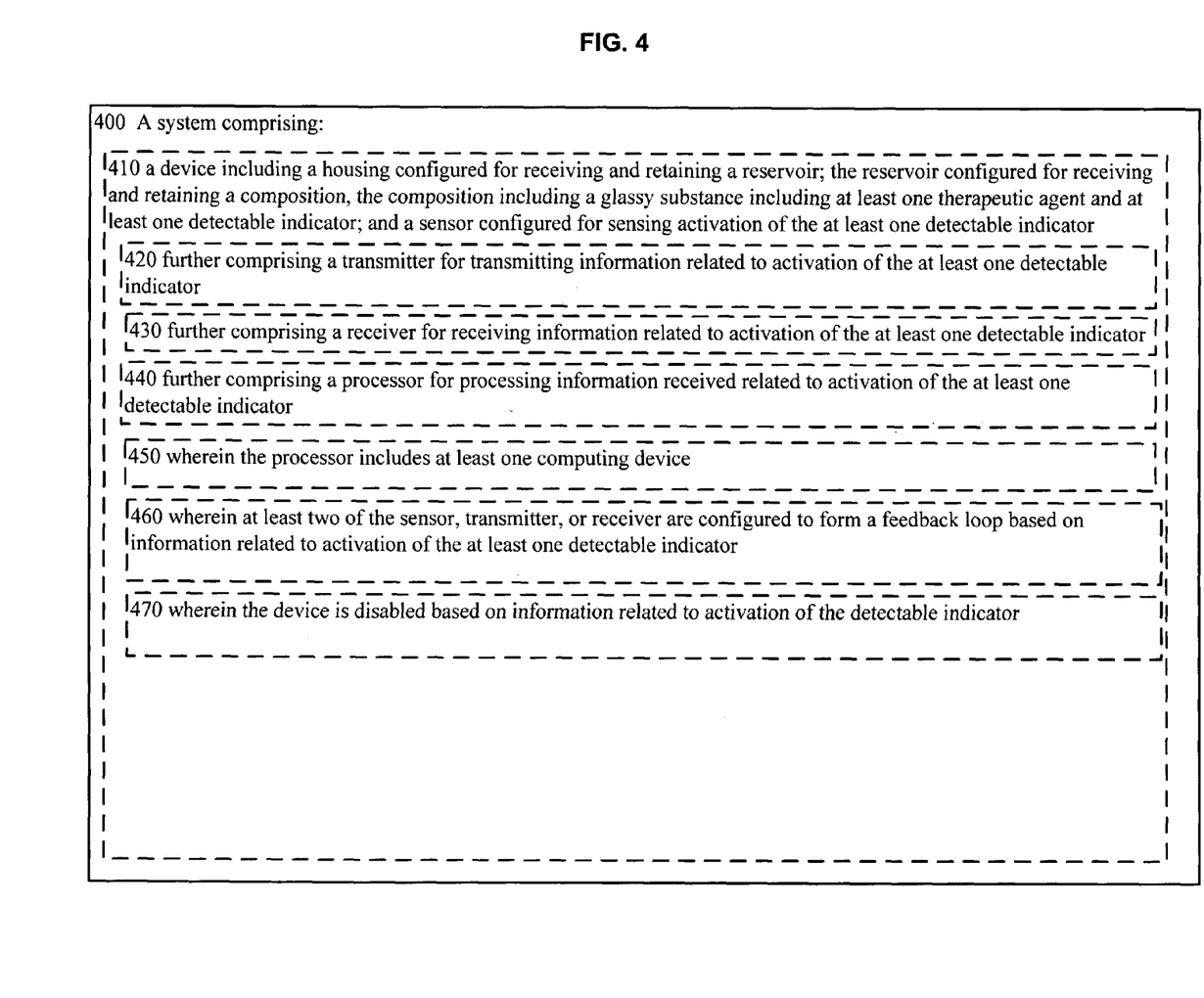
FIG. 4 is a partial view of an embodiment of a system disclosed herein.

As depicted in FIG. 4, in an embodiment, a system 400 including 410 a device including a housing configured for receiving and retaining a reservoir; the reservoir configured for receiving and retaining a composition, the composition including a glassy substance including at least one therapeutic agent and at least one detectable indicator; and a sensor configured for sensing activation of the at least one detectable indicator. In an embodiment 420, the system 400 further comprises 420 a transmitter for transmitting information related to activation of the at least one detectable indicator. In an embodiment, the system 400 further comprises 430 a receiver for receiving information related to activation of the at least one detectable indicator. In an embodiment, the system 400 further comprises 440 a processor for processing information received related to activation of the at least one detectable indicator. In an embodiment 450, the processor includes at least one computing device. In an embodiment 460, at least two of the sensor, transmitter, or receiver are configured to form a feedback loop based on information related to activation of the at least one detectable indicator. In an embodiment 470, the device is disabled based on information related to activation of the detectable indicator.

Figure 5:
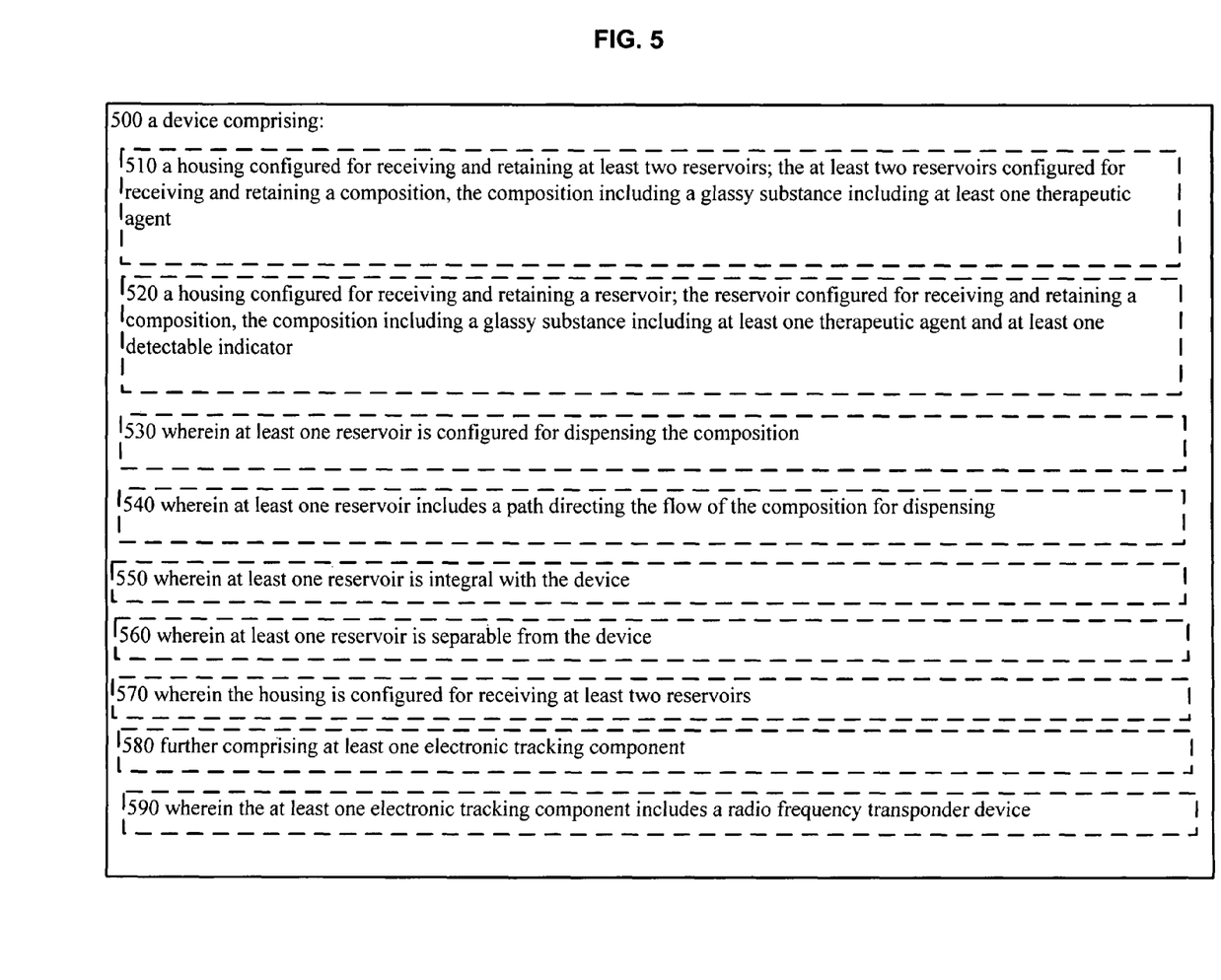
FIG. 5 is a partial view of an embodiment of a device disclosed herein.

As depicted in FIG. 5, a device 500 comprises 510 a housing configured for receiving and retaining at least two reservoirs; the at least two reservoirs configured for receiving and retaining a composition, the composition including a glassy substance including at least one therapeutic agent. In an embodiment 520, a housing configured for receiving and retaining a reservoir; the reservoir configured for receiving and retaining a composition, the composition including a glass substance including at least one therapeutic agent and at least one detectable indicator. In an embodiment 530, at least one reservoir is configured for dispensing the composition. In an embodiment 540, at least one reservoir includes a path directing the flow of the composition for dispensing. In an embodiment 550, at least one reservoir is integral with the device. In an embodiment 560, at least one reservoir is separable from the device. In an embodiment 570, the housing is configured for receiving at least two reservoirs. In an embodiment 580, the device 500 further comprises 580 at least one electronic tracking component. In an embodiment 590, the at least one electronic tracking component includes a radio frequency transponder device.

Figure 6:
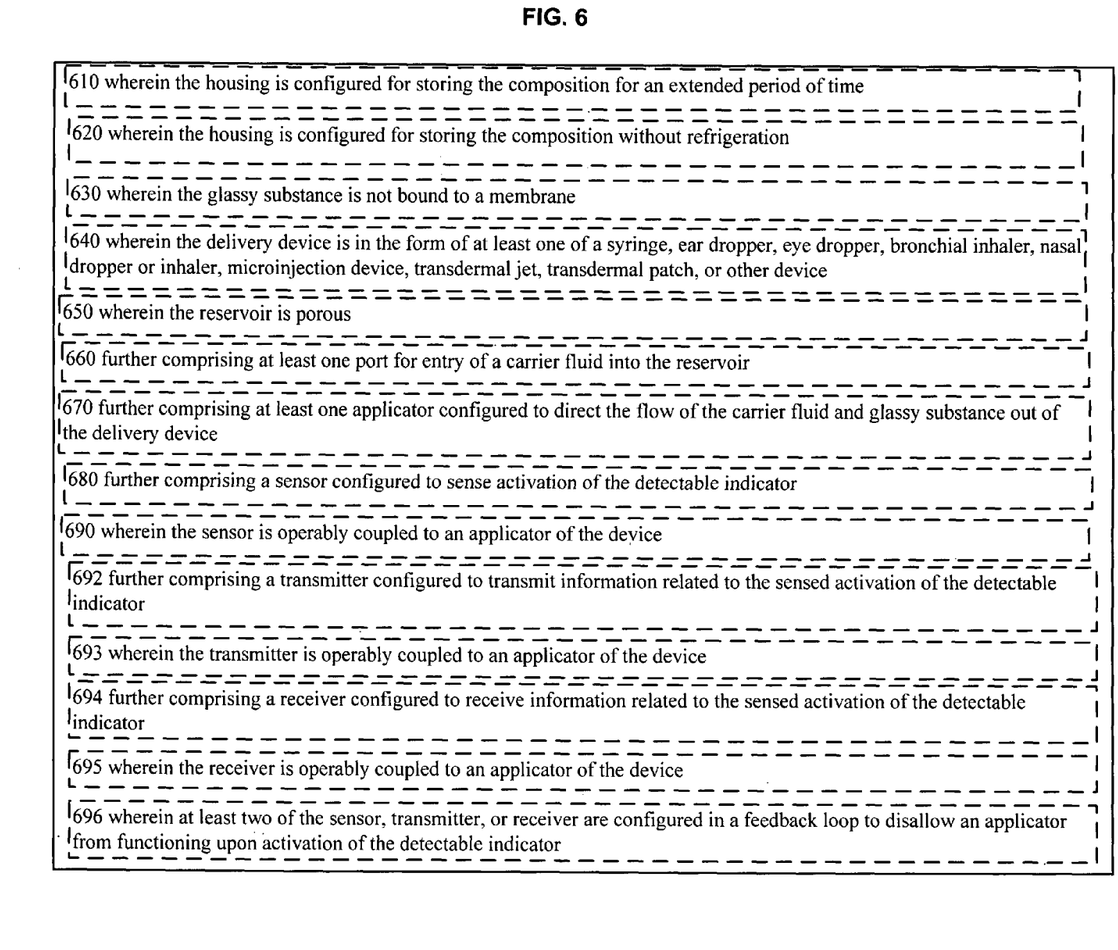
FIG. 6 is a partial view of the embodiment of FIG. 5.

As depicted in FIG. 6, in an embodiment 610, the housing is configured for storing the composition for an extended period of time. In an embodiment 620, the housing is configured for storing the composition without refrigeration. In an embodiment 630, the glassy substance is not bound to a membrane. In an embodiment 640, the delivery device is in the form of at least one of a syringe, ear dropper, eye dropper, bronchial inhaler, nasal dropper or inhaler, microinjection device, transdermal jet, transdermal patch, or other device. In an embodiment 650, the reservoir is porous. In an embodiment 660, the device further comprises at least one port for entry of a carrier fluid into the reservoir. In an embodiment 670, the device further comprises at least one applicator configured to direct the flow of the carrier fluid and glassy substance out of the delivery device. In an embodiment 680, the device further comprises a sensor configured to sense activation of the detectable indicator. In an embodiment 690, the sensor is operably coupled to an applicator of the device. In an embodiment 692, the device further comprises a transmitter configured to transmit information related to the sensed activation of the detectable indicator. In an embodiment 693, the transmitter is operably coupled to at least one applicator of the device. In an embodiment 694, the device further comprises a receiver configured to receive information related to the sensed activation of the detectable indicator. In an embodiment 695, the receiver is operably coupled to at least one applicator of the device. In an embodiment 696, at least two of the sensor, transmitter, or receiver are configured in a feedback loop to disallow an applicator from functioning upon activation of the detectable indicator.

PROPHETIC EXAMPLES

Prophetic Example 1

A Thermostable Influenza Vaccine with Visual Indicator

An influenza vaccine is formulated as a glassy substance that contains an indicator to detect hydration of the vaccine (which indicates that the integrity or quality of the vaccine has been compromised). The vaccine is made as an amorphous glassy substance that is stable for extended periods at a tropical temperature, and that can be reconstituted with a buffer solution just prior to administration. The thermostable influenza vaccine can be transported and stored without refrigeration, and reconstituted rapidly in the event of a flu pandemic. Moreover, a color indicator alerts healthcare workers that the vaccine has been compromised by hydration during transport or storage.

A subunit vaccine is produced as a glassy substance containing: trehalose, a hemagglutinin (HA) polypeptide from influenza virus, and a moisture sensor. A glassy substance vaccine is formed by freeze-drying solutions of trehalose (see e.g., Amorij et al., Vaccine 25: 6447-6457, 2007 which is incorporated herein by reference). A vaccine solution containing: 1) approximately 1.7% (w/v) trehalose (available from Sigma-Aldrich, St. Louis, Mo.), 2) approximately 360 µg/ml of influenza HA protein (e.g., Influenza Hemagglutinin H1N1 A/California available from Sino Biological Inc., Beijing 100176, P.R. China), and 3) a chemical indicator of moisture exposure (i.e., moisture sensor) are frozen in liquid nitrogen for 5-10 minutes and freeze-dried. A freeze-dryer (e.g., Heto PowerDry PL6000 available from Thermo Fisher Scientific, Waltham, Mass.) is set to a shelf temperature of −35° C., a condenser temperature of −55° C. and a pressure of 0.220 mbar. After 24 hours the pressure is lowered to 0.060 mbar and the shelf temperature is gradually increased to 20° C. and maintained for 24 hours. The dry vaccine samples are transferred to a vacuum desiccator at room temperature.

A chemical indicator of cumulative moisture exposure is incorporated in the glassy substance vaccine. Compositions and methods for moisture sensors are described (see e.g., U.S. Patent Application No. 2009/0035865, which is incorporated herein by reference). For example, ferric sulfate ($Fe_2(SO4)_3.5H_2O$) is dissolved in the vaccine solution at a concentration of 25% (w/v) prior to freeze drying the vaccine solution as described above. The dry vaccine samples, containing ferric sulfate are overlaid with a solution of tetrabutylammonium thiocyanate (50% w/v) dissolved in dichloromethane. The vaccine samples are dried at 37° C. for approximately 15 minutes to evaporate the dichloromethane, and then stored in a dessicator at room temperature. If, during transport or storage, the dry vaccine samples are exposed to moisture, then any water adsorbed allows reaction of ferric sulfate and tetrabutylammonium thiocyanate to form ferric thiocyanate ($[Fe(SCN)(H2O)_5]^{2+}$ which displays a blood red color. This moisture indicator can be detected visually, or by using a spectrophotometer, and measuring absorbance of the vaccine sample at 480 nm wavelength.

The glassy substance vaccine with moisture indicator is formed within a drug delivery device for shipping and storage. For example 1.0 mL plastic syringes with plastic caps in place of needles are filled with approximately 0.5 ml of the vaccine solution containing trehalose, HA protein and ferric sulfate. The vaccine aliquots are freeze-dried and then overlaid with tetrabutylammonium thiocyanate, and heated to 37° C. The glassy substance vaccine is transported and stored in syringes which are transparent, to allow visualizing the moisture indicator. For immunization the glassy substance vaccine is reconstituted in the syringe with approximately 0.5 ml of sterile water and an approximately 25 gauge needle is attached to the syringe for subcutaneous injection.

Prophetic Example 2

Attenuated Viral Vaccine Composition Stabilized as a Glassy Substance with an Indicator to Detect Time and Temperature Exposure of the Vaccine An attenuated viral vaccine is formulated as a glassy substance that also contains an indicator to detect the exposure of the vaccine to elevated temperature (which indicates that the integrity or quality of the vaccine could have been compromised). The vaccine is made as an amorphous glassy substance and it is stable for extended periods at elevated temperatures (e.g., greater than 30° C.), and it is reconstituted with a buffer solution just prior to administration. The thermostable viral vaccine is transported and stored without refrigeration, and reconstituted rapidly in the event of a viral pandemic. Moreover, a color indicator alerts healthcare workers if the vaccine has been compromised by exposure to elevated temperatures and/or extended times during transport or storage.

An attenuated viral vaccine is produced as a glassy substance containing sucrose, trehalose and a time and temperature indicator. Attenuated viral vectors are formulated with solutions containing sucrose and trehalose and then desiccated to create a glassy substance. Methods to stabilize an attenuated DNA virus in a glassy substance are described (see e.g., Alcock et al., Sci. Transl. Med. 2: 19ra12, 2010, which is incorporated herein by reference). For example, a modified vaccinia virus Ankara (MVA), which encodes antigens from a pathogen such as human immunodeficiency virus (see e.g., Hanke et al., J. Gen. Virol. 88: 1-12, 2007, which is incorporated herein by reference) is grown on chick embryo fibroblasts and purified to obtain a viral stock. The MVA stock is diluted five-fold in a solution containing 0.25 M sucrose and 0.25 M trehalose and the MVA/sugar solution is pipetted onto a membrane (e.g., a S14 glass fiber (GF) membrane available from Whatman Inc., Piscataway, N.J.) prior to desiccation. Approximately 55 µl of a MVA/sugar solution containing approximately $4 \times 10^8$ $CCID_{50}$ (50% cell culture infectious dose) are pipetted onto a GF membrane and the membrane is dried overnight (approximately 18 hours) at 20° C. to 25° C. with a silica gel bed to control the humidity between 10% and 20% relative humidity. The dried membranes are maintained under low humidity conditions (between about 2% and 10% relative humidity).

A time and temperature indicator is incorporated into the glassy substance vaccine by layering reactive chemicals and an indicator onto the glassy substance. Methods and compositions to create a solid state indicator that monitors time and temperature have been described (see e.g., U.S. Pat. No. 5,254,473, which is incorporated herein by reference). A time and temperature indicator is prepared by combining: 1 ml of 5% (v/v) cellulose acetate butyrate in methylethylketone, 10 mg of methyl green dye (a pH indicator) and 0.25 ml of 30% dodecylamine (a base) in methylethylketone. The chemical mixture is layered onto the glassy substance/membrane using a wet film applicator. The membranes containing the glassy substance vaccine with indicator are allowed to dry, leaving a solid state indicator that is transparent until it is exposed to sufficient temperatures for sufficient time to allow a reaction to occur and alter the pH, thus causing the methyl green pH indicator to turn violet. For example, exposure of the time and temperature indicator to room temperature (approximately 22° C.) for approximately 21 days results in a complete color change to violet, but exposure to 60° C. requires only 8 hours for a complete color change by the indicator. The indicator is monitored visually or with a spectrophotometer. Using a spectrophotometer the extent of the reaction can be monitored based on the absorbance at wavelengths between approximately 400 nm-450 nm. A solid state time and temperature indicator is designed by choosing specific chemicals that determine the time and temperature required to cause a color change. For example, if the glass transition temperature for a glassy substance vaccine is 50° C. (see e.g., Alcock et al., Ibid.), then a temperature indicator that changes color when exposed to 50° C. for 1 minute is designed (see e.g., U.S. Pat. No. 5,254,473, Ibid, incorporated herein by reference).

The glassy substance vaccine is compromised by exposure to high temperatures that exceed the glass transition temperature of the glassy substance, and if attenuated virus vaccines with a temperature indicator are transported and stored in remote locations, temperature may not be controlled. A solid state temperature indicator alerts healthcare personnel if the vaccine has been compromised before it is administered. Also the absence of color in the indicator can provide assurance that the vaccine has been shipped and stored properly at appropriate temperatures.

Prophetic Example 3

Therapeutic Protein, Interferon Alpha is Stabilized as an Amino Acid/sucrose Glass and Stored in a Delivery Device with an Indicator to Detect any Loss of Biological Activity if the Protein is Exposed to Extreme Environmental Conditions Interferon-alpha (IFN-α) is formulated as part of a glassy substance that also contains an indicator enzyme to detect deactivation of the cytokine (indicating that the integrity or quality of the therapeutic agent has been compromised). The indicator enzyme catalyzes reactions leading to formation of a colored dye when the IFN-α glassy substance is dissolved in an assay buffer. The indicator assures healthcare workers that IFN-α has not been compromised during transport or storage. The thermostable IFN-α can be transported and stored without refrigeration, and reconstituted rapidly in the event of a viral outbreak IFN-α, a therapeutic protein with antiviral activity, is stabilized as a glassy substance that contains an indicator enzyme to detect loss of biological activity by the therapeutic protein that may occur during storage or transport. IFN-α is produced as a glassy substance containing sucrose, amino acids, and an indicator enzyme, lactic dehydrogenase (LDH). IFN-α and LDH are formulated as a solution containing: sucrose, L-arginine, and L-phenylalanine that is spray-dried to create a glassy substance. Methods to stabilize proteins in a glassy substance are described (see e.g., U.S. Pat. No. 6,689,755, which is incorporated herein by reference). For example, a solution containing 240 μg/mL of pegylated interferon alpha-2b (available from Schering-Plough Corp., Kenilworth, N.J.) and approximately 0.01 μg/mL of human LDH (available from Sigma-Aldrich, St. Louis, Mo.; see Lactic Dehydrogenase Data Sheet which is incorporated herein by reference) is supplemented with sucrose (50 mg/mL), L-arginine (10 mg/mL) and L-phenylalanine (10 mg/mL).

The solution containing amino acids, sucrose, IFN-α and the indicator enzyme, LDH is adjusted to a pH of 7.4 and spray-dried to produce an amorphous glassy substance. Methods and conditions for spray-drying protein solutions are described (see e.g., U.S. Pat. No. 6,689,755, Ibid.). For example an inlet air temperature of approximately 100° C. to 140° C. and a residual moisture content of less than about 4% are optimal to obtain glassy substances with glass transition temperatures (Tg) greater than about 40° C. The Tg is the temperature at which an amorphous solid is converted from the glassy state into the fluid or viscous state and vice versa. When the Tg is exceeded, a glassy substance is converted to a fluid and the stability of the agents contained in the glassy substance may be compromised. Glassy substances with Tg greater than 40° C. or 50° C. stabilize the agents at extreme temperatures (e.g., ≧35° C.) and for prolonged periods at room temperature (e.g., approximately 20 days at about 22° C.). The Tg for a glassy substance can be determined by differential scanning calorimetry. Methods and equipment for differential scanning calorimetry to measure Tg for glassy substances are described in U.S. Pat. No. 6,689,755, Ibid.

The enzyme LDH serves as an indicator for denaturation, degradation and deactivation of IFN-α since, like IFN-α, LDH is deactivated by elevated temperatures, freeze-thawing and storage at room temperature (see LDH Assay Sheet which is incorporated herein by reference). To assess the viability of IFN-α formulated with LDH in a glassy substance the glassy substance is dissolved in an LDH buffer solution that contains a colorimetric substrate for LDH. For example, a LDH assay kit (available from Cayman Chemical Co., Ann Arbor, Mich.; see LDH Assay Sheet, Ibid.) contains a LDH assay buffer with: NAD+ (a cofactor), Lactic Acid (substrate), INT (tetrazolium salt) and diaphorase (an enzyme to catalyze reduction of INT). Enzymatically active LDH, present in the glassy substance catalyzes reactions that lead to the formation of a highly colored formazan dye which absorbs strongly at approximately 490 nm. Since the substrate, lactic acid (at approximately 50 mmole/L) and cofactor NAD+ (at approximately 0.478 mmole/L) are present in excess, the amount of active LDH enzyme recovered from the glassy substance can be determined in a zero order reaction by measuring the absorbance at 490 nm ($A_{490}$) with a spectrophotometer. Methods, reagents and calculations to measure human LDH enzymatic activity are described (see e.g., Nisselbaum et al., J. Biol. Chem. 238: 969-974, 1963 which is incorporated herein by reference). For example, approximately 1 mU (about 0.011 μg) of LDH incubated 30 minutes at room temperature will generate an $A_{490}$ of approximately 0.7 in this assay system.

To evaluate the percentage of LDH activity remaining in the glassy substance, a positive control sample containing IFN-α, sucrose, amino acids, LDH and LDH assay buffer is used to determine the absorbance corresponding to 100% LDH activity and also a standard curve for LDH enzyme activity as described (see e.g., LDH Assay Sheet, Ibid.). Based on the standard curve, the percentage of input LDH enzyme activity recovered from the glassy substance can be determined.

To correlate the survival of IFN-α and LDH when co-formulated as a glassy substance, the bio-activity of IFN-α is determined before and after formulation as a glassy substance and with or without exposure to elevated temperatures. An assay kit for Interferon bioactivity, available from PBL InterferonSource, Piscataway, N.J. (see Interferon Assay Sheet which is incorporated herein by reference) is used to measure IFN-α bioactivity. For example, IFN-α combined with LDH, sucrose, amino acids and LDH assay buffer is tested in a gene reporter bioassay that measures bioluminescence generated by luciferase to determine the amount of interferon activity. The IFN-α solution prior to spray-drying is used to establish a standard curve for IFN-α bio-activity. The glassy substance containing IFN-α is subjected to elevated temperatures prior to assaying for interferon bioactivity. For example, separate aliquots of the glassy substance are heated to 25° C. or 30° C. or 35° C. or 40° C. or 45° C. or 50° C. or 55° C. for 10 minutes, or 60 minutes or 4 hours and then dissolved in assay buffer and assayed for interferon bioactivity. Portions of the same aliquots of glassy substance are also assessed for LDH enzymatic activity as reflected in the absorbance of formazan dye at 490 nm (see above). Graphs of IFN bioactivity versus temperature are compared with plots of LDH activity versus temperature to correlate the IFN bioactivity corresponding to a given level of LDH enzymatic activity. Comparisons of thermal stability for different proteins are described (see e.g., Fields and Somero, *Proc. Natl. Acad. Sci. USA* 95: 11476-11481, 1998 which is incorporated herein by reference). For example, a glassy substance heated to 50° C. for 60 minutes may retain 80% of LDH enzymatic activity and 90% of IFN bio-activity.

The glassy substance containing IFN-α and the indicator enzyme, LDH is spray-dried and collected as a powder in a drug delivery device for shipping and storage. For example a 1.0 mL plastic syringe with plastic caps at the ends in place of needles and plungers is filled with approximately 50 mg of powdered glassy substance corresponding to approximately 120 μg of pegylated IFN-α2b. The glassy substance IFN-α is transported and stored in the syringes which are transparent to allow visible light transmittance. Prior to administration, the glassy substance IFN-α is reconstituted in the syringe with approximately 0.5 ml of LDH assay buffer, incubated for approximately 10 minutes at room temperature and the absorbance at 490 nm is read in a portable spectrophotometer (e.g., a Spectronic™ 20 available from Cole-Parmer, Vernon Hills, Ill.).

The spectrophotometer reports the $A_{490}$ value to a computer, and the computer determines the relative percentage of IFN-α bioactivity in the syringe based on the $A_{490}$ detected. The percentage of initial IFN-α bioactivity corresponding to LDH enzymatic activity (i.e. $A_{490}$) is determined for each lot of IFN-α as described above. The correlation data, IFN-α lot number and IFN-α bioactivity criteria (e.g., minimal percentage of input bioactivity approved for injection) are stored in the computer and linked by a radio frequency identification (RFID) tag present on each syringe. RFID systems for tracking biological samples and corresponding stored information are described. (See e.g., U.S. Patent Publication No. 2008/0268514 A1, which is incorporated herein by reference.) For example a RFID tag on the syringe signals to a RFID reader, which signals to a linked computer where $A_{490}$ data is evaluated and bioactivity criteria (i.e., a previously established minimum level of IFN bio-activity) are applied. If activity criteria are met the computer signals to authorize administration of the IFN-α solution, and the syringe caps are replaced by a 25 gauge needle and a syringe plunger to allow injection of the IFN-α.

Prophetic Example 4

Therapeutic Protein, Insulin, is Stabilized with a Glassy Substance in a Microinjection Device that Includes an Indicator to Detect Loss of Biological Activity in the Insulin and an Electronic Tracking Component Insulin is formulated as part of a glassy substance that also contains an indicator enzyme to detect the loss of bioactivity by insulin. Prior to injection, the insulin glassy substance is dissolved in an assay buffer, and the indicator enzyme catalyzes reactions leading to formation of a colored dye. The indicator dye is detected by the microinjection device which determines whether the insulin is active prior to injection. The microinjection device blocks or allows injection of the insulin dose based on the absorbance of the indicator dye it detects. The microinjection device contains multiple doses of insulin stabilized as a glassy substance, and the device can be transported and stored without refrigeration. The microinjection device with glassy substance insulin, an indicator enzyme, and a dye detector also contains an electronic tracking component, a radio frequency identification tag.

A therapeutic protein, insulin is stabilized as a glassy substance in a microinjection device and contains an indicator enzyme to detect loss of insulin biological activity that may occur during transport, storage or use of the device. Insulin is produced as a glassy substance containing sucrose, amino acids and indicator enzymes, lactic dehydrogenase (LDH) and diaphorase. Insulin, LDH and diaphorase are formulated in a solution containing: sucrose, L-arginine, and L-phenylalanine that is spray-dried to create a glassy substance. Methods to stabilize proteins in a glassy substance are described (see e.g., U.S. Pat. No. 6,689,755 which is incorporated herein by reference). For example, a solution containing 100 IU (international units)/mL of human insulin (available from Novo-Nordisk, Bagsvaerd, Denmark); approximately 0.01 μg/mL of human LDH (available from Sigma-Aldrich, St. Louis, Mo.; see Lactic Dehydrogenase Data Sheet which is incorporated herein by reference) and 0.05 μg/mL human diaphorase (available from Sigma-Aldrich, St. Louis, Mo.; see Diaphorase Specification Sheet which is incorporated herein by reference) is supplemented with sucrose (50 mg/mL), L-arginine (10 mg/mL) and L-phenylalanine (10 mg/mL). The solution containing amino acids, sucrose, insulin and the indicator enzymes is adjusted to a pH of 7.4 and spray-dried to produce an amorphous glassy substance. Methods and conditions for spray-drying protein solutions are described (see e.g., U.S. Pat. No. 6,689,755, Ibid). For example an inlet air temperature of approximately 100° C. to 140° C., and a residual moisture content of less than about 4% are optimal to obtain glassy substances with glass transition temperatures (Tg) greater than about 40° C. The Tg is the temperature at which an amorphous solid is converted from the glassy state into a fluid or viscous state. When the Tg is exceeded a glassy substance is converted to a fluid, and the stability of the agents contained in the glassy substance may be compromised. Glassy substances with Tg greater than 40° C. or 50° C. stabilize the agents at high temperatures (e.g., ≧35° C.) and also for prolonged periods at room temperature (e.g., approximately 20 days at about 22° C.). The Tg for a glassy substance can be determined by differential scanning calorimetry. Methods and equipment for differential scanning calorimetry are described in U.S. Pat. No. 6,689,755, Ibid.

The enzyme LDH serves as an indicator for denaturation, degradation and deactivation of insulin. LDH is deactivated by elevated temperatures, freeze-thawing and extended storage at ambient temperatures (see LDH Assay Sheet, which is incorporated herein by reference). To assess the viability of insulin formulated with LDH in a glassy substance, the glassy substance is dissolved in an LDH assay buffer solution that contains a colorimetric substrate for LDH. For example, a LDH assay kit (available from Cayman Chemical Co., Ann Arbor, Mich.; see LDH Assay Sheet, Ibid.) contains a LDH assay buffer with: NAD+ (a cofactor), Lactic Acid (substrate), INT (tetrazolium salt) and diaphorase (an enzyme to catalyze reduction of INT). Enzymatically active LDH, present in the glassy substance catalyzes reactions that lead to the formation of a highly colored formazan dye which absorbs strongly at a wavelength of approximately 500 nanometers (nm). Since the substrate, lactic acid (at approximately 50 mmole/L) and cofactor NAD+ (at approximately 0.478 mmole/L) are present in excess, the amount of active LDH enzyme recovered from the glassy substance is determined from a zero order reaction by measuring the absorbance at approximately 500 nm ($A_{500}$) by spectroscopy. Methods, reagents and calculations to measure human LDH enzymatic activity are described (see e.g., Nisselbaum et al., *J. Biol. Chem.* 238: 969-974, 1963, which is incorporated herein by reference). For example, approximately 1 mU (about 0.011 μg) of LDH incubated 30 minutes at room temperature will generate an $A_{490}$ of approximately 0.7 in this assay system. To establish a reference value for calculating LDH activity, a liquid positive control sample containing insulin, sucrose, amino acids, LDH, diaphorase and LDH assay buffer is used to determine the absorbance corresponding to 100% LDH activity and also to establish a standard curve for LDH enzyme activity (see e.g., LDH Assay Sheet, Ibid.). Based on the standard curve, the percentage of input LDH enzyme activity recovered from the glassy substance can be determined.

To determine the stability of insulin and LDH, the bioactivity of both proteins is determined after formulation as a glassy substance and exposure to elevated temperatures. An insulin assay kit (available from HTRF Cisbio US, Bedford, Mass.; see Insulin Assay Sheet which is incorporated herein by reference) is used to measure immunoreactive insulin. The glassy substance containing insulin is dissolved in LDH assay buffer and assayed for immunoreactive insulin after exposure to elevated temperatures for various times. For example, separate aliquots of the glassy substance are heated to 20° C., or 25° C., or 30° C., or 35° C., or 40° C., or 45° C., or 50° C., or 55° C., for 10 minutes, or 60 minutes, or 4 hours, and then dissolved in LDH assay buffer and assayed for insulin. An aliquot of the glassy substance not subjected to elevated temperature is tested for insulin immunoreactivity immediately after dissolving in LDH assay buffer to establish a reference value for 100% insulin immunoreactivity.

In parallel, portions of all samples of glassy substance are tested for LDH enzymatic activity as reflected in the absorbance of formazan dye at 500 nm (see above). Graphs of insulin immunoreactivity versus temperature are compared with plots of LDH activity versus temperature to correlate insulin immunoreactivity and LDH enzymatic activity. Methods to compare thermal stability for different proteins are described (see e.g., Fields and Somero, *Proc. Natl. Acad. Sci. USA* 95: 11476-11481, 1998 which is incorporated herein by reference). For example, a glassy substance heated to 50° C. for 60 minutes may retain 80% of LDH enzymatic activity and 90% of insulin immunoreactivity.

A microinjection device is used to transport, store and deliver multiple doses of the insulin glassy substance. Multiple doses (e.g., approximately 25 doses of 1 IU each) of insulin with indicator enzymes are stored as a glassy substance in individual compartments of the device and connected by channels to a reservoir containing LDH Assay buffer, microcircuitry, valves, and a pump control; the delivery of LDH assay buffer to dissolve the insulin glassy substance, and the delivery of the insulin solution to the patient. The device also contains a miniature spectroscopy system, and electronic circuitry to measure the absorbance of the LDH colorimetric substrate, and to calculate the immune reactivity of the insulin prior to activating valves to effect subcutaneous injection of the insulin solution. A microinjection device with reservoirs, channels, valves, and a pump to deliver an insulin solution subcutaneously is described (see e.g., U.S. Pat. No. 7,713,262, which is incorporated herein by reference). The microinjection device is constructed using soft lithography methods to create chambers, channels, valves, reservoirs, and pumps (see e.g., Unger et al. *Science* 288: 113-116, 2000 and Liu et al. *Lab Chip* 9: 1200-1205, 2009 (Abstract) which are incorporated herein by reference). For example, a microinjection device is constructed with 25 chambers that each contains approximately 20 mg of glassy substance containing approximately 1 IU of insulin. Each chamber is connected via a valve to an input channel leading to a pump and a reservoir containing LDH assay buffer. A controller activates the valve and the pump to provide LDH assay buffer to a chamber where the insulin glassy substance is dissolved and analyzed for bioactivity using the indicator enzymes and a miniature spectroscopy system.

The microinjection device contains a miniature spectroscopy system that determines the immune reactivity of the insulin glassy substance by monitoring the indicator enzyme LDH. A miniature spectroscopy system is built into the microinjection device to measure absorbance at a wavelength of approximately 500 nanometers ($A_{500}$) corresponding to the absorbance maximum for formazan dye that indicates LDH enzyme activity. Methods and materials to construct a miniature spectroscopy system are described. See e.g., Adams et al., *Sensors and Actuators A* 104: 25-31, 2003 which is incorporated herein by reference. The microinjection device is constructed from a silicon elastomer (e.g., polydimethylsiloxane) with microfluidic chambers (approximately 1 mm wide and 2 mm deep and 20 mm long) placed directly over complementary metal oxide semiconductor (CMOS) silicon detector arrays, and illuminated from above by a Silicon Carbide/Gallium Nitride Blue Green light emitting diode with a wavelength maximum of 505 nm. (CMOS detector arrays and light emitting diodes are available from OSI Optoelectronics, Hawthorne, Calif.) The CMOS detector signals to electronic microcircuitry in the device which calculates the $A_{500}$ of the colorimetric substrate and the corresponding immune reactivity of the insulin in the chamber. If minimum bioactivity criteria are met the microinjection device actuates an export pump, and opens the export valve to deliver the insulin solution subcutaneously to the patient. Conversely if the insulin does not display minimum bioactivity the device controller closes the valves for the chamber, and alerts the patient and caregiver with a signal light.

Prophetic Example 5

Microinjection Device for Administering Multiple Glassy Substance Vaccines

A microinjection device can deliver multiple vaccines stabilized as glassy substances and formulated with indicator enzymes, as described herein. In this embodiment, the microinjection device has a modular construction that facilitates administration of multiple different glassy substance vaccines with the device.

A microinjection device is used to deliver multiple glassy substance vaccines. Vaccines targeting different pathogens (e.g., influenza A H1N1, influenza A H3N2, influenza B (Brisbane), Hepatitis B virus, meningococci, measles, mumps and rubella; see e.g., CDC Vaccine Schedule which is incorporated herein by reference) are formulated as glassy substances containing moisture, time and temperature indicators. (See Examples 1 and 2 above for methods and compositions to formulate subunit vaccines and attenuated viral vaccines as glassy substances with indicators.)

Individual vaccines (e.g., hepatitis B virus vaccine or influenza A H1N1) and combinations of vaccines (e.g., influenza A H1N1, influenza A H3N2, influenza B (Brisbane)) are produced as glassy substances with indicators and deposited in arrays comprised of modules containing a single dose of a vaccine. For example an array may contain approximately 24 modules with each module containing a single dose of a glassy substance flu vaccine (e.g., influenza A H1N1), and a second array may contain 24 modules each containing a single dose of a different flu vaccine (e.g., influenza A H3N2). The microinjection device accepts modules containing different vaccines and facilitates delivery of multiple vaccines. Vaccine modules are used to transport and store glassy substance vaccines with indicators, and they are fabricated from biocompatible plastic with an inlet port and an outlet port that interface with corresponding ports in the microinjection device. The specific vaccine module, vaccine lot number, manufacture date and indicator data are stored in a computer and linked by a radio frequency identification (RFID) tag present on each vaccine module. RFID systems for tracking biological samples and corresponding stored information are described. (See e.g., U.S. Patent Publication No. 2008/0268514 A1 which is incorporated herein by reference.)

A viable glassy substance vaccine module (as indicated by an unchanged time and temperature indicator; i.e., no color change) is inserted in the microinjection device connecting the inlet and outlet ports with the corresponding ports in the device. A microinjection device with reservoirs, channels, valves, and a pump to deliver biologic solutions subcutaneously is described (see e.g., U.S. Pat. No. 7,713,262 which is incorporated herein by reference). The microinjection device is constructed using soft lithography methods to create chambers, ports, channels, valves, reservoirs, and pumps (see e.g., Unger et al. *Science* 288: 113-116, 2000 and Liu et al. *Lab Chip* 9: 1200-1205, 2009 (Abstract), each of which is incorporated herein by reference).

The microinjection device is constructed with 1 or more chambers that accept vaccine modules. Each chamber is connected via a valve to an inlet channel leading to a pump and a reservoir containing sterile water. A controller activates the valve and the pump to provide sterile water from a reservoir via the inlet port to the vaccine module where the vaccine glassy substance is dissolved and then pumped through the outlet port to be delivered subcutaneously. The used vaccine module is discarded, and another vaccine module is inserted in the microinjection device to administer a different vaccine. Multiple vaccine module arrays containing glassy substance vaccines with indicators for a number of pathogens (e.g. multiple strains of influenza virus, measles, mumps, rubella, Hepatitis B virus and others) can be stored and administered as needed individually or in combination using the microinjection device. Signals from the RFID device associated with each vaccine module to the computer can identify the date, time and type of vaccine administered.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A composition comprising:
   a glassy substance including at least one of sucrose, glucose, fructose, maltose, mannose, maltulose, iso-maltose, nigerose, cellubiulose, turanose, panose, isomaltotriose, stachyose, nystose, maltotetrose, maltopentose, maltohexose, malopheptose, ubombo sugar, raffinose, arabinose, galactose, xylose, melibiose, salicin, arbutin, arabinose, adonitol, sorbose, thamnose, destrose, dulcitol, melezitose, gentiobiose, lyxose, tagatose, fucose, arabitol, or trehalose,
   a vaccine, and
   a moisture sensor including two components that react with each other upon degradation of the glassy substance; wherein the two components include ferric sulfate and tetrabutylammonium thiocyanate.

2. A composition comprising:
   a glassy substance including at least one of sucrose, glucose, fructose, maltose, mannose, maltulose, iso-maltose, nigerose, cellubiulose, turanose, panose, isomaltotriose, stachyose, nystose, maltotetrose, maltopentose, maltohexose, malopheptose, ubombo sugar, raffinose, arabinose, galactose, xylose, melibiose, salicin, arbutin, arabinose, adonitol, sorbose, thamnose, destrose, dulcitol, melezitose, gentiobiose, lyxose, tagatose, fucose, arabitol, or trehalose,
   insulin, and
   a detectable indicator of degradation of the glassy substance including the enzyme LDH.

3. The composition of claim 2, further including at least one detectable indicator includes at least one of phenol red, ethidium bromide, DNA polymerase, cobalt chloride, Reichardt's dye, a restriction endonuclease, or fluorogenic protease substrate.

4. The composition of claim 2, further including at least one carrier fluid.

5. The composition of claim 4, wherein the carrier fluid includes at least one phase of water, saline, intravenous fluid, or other fluid.

6. The composition of claim 2, further including at least one preservative.

7. The composition of claim 6, wherein the at least one preservative includes at least one enzyme inhibitor.

8. The composition of claim 6, wherein the at least one preservative includes at least one of validamycin A, TL-3, sodium orthovanadate, sodium fluoride, N-alpha-tosyl-Phe-chloromethylketone, N-alpha-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

9. The composition of claim 6, wherein the preservative includes a cryoprotectant.

10. The composition of claim 2, further including at least one buffer.

11. The composition of claim 10, wherein the at least one buffer includes at least one of bicarbonate, monosodium phosphate, disodium phosphate, or magnesium oxide.

12. The composition of claim 2, wherein the composition includes at least two layers.

13. The composition of claim 12, wherein the at least two layers include at least one first glassy substance layer including the therapeutic agent that is different from at least one second glassy substance layer that includes the detectable indicator.

14. The composition of claim 2, wherein the at least one detectable indicator indicates degradation or disruption of the glassy substance by at least one of a change in color, change in opacity, or change in light scattering.

15. The composition of claim 1, further including at least one carrier fluid.

16. The composition of claim 15, wherein the carrier fluid includes at least one phase of water, saline, intravenous fluid, or other fluid.

17. The composition of claim 1, further including at least one preservative.

18. The composition of claim 17, wherein the at least one preservative includes at least one enzyme inhibitor.

19. The composition of claim 18, wherein the at least one preservative includes at least one of validamycin A, TL-3, sodium orthovanadate, sodium fluoride, N-alpha-toysl-Phe-chloromethylketone, N-alpha-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

20. The composition of claim 1, further including at least one buffer.

21. The composition of claim 20, wherein the at least one buffer includes at least one of bicarbonate, monosodium phosphate, disodium phosphate, or magnesium oxide.

* * * * *